United States Patent
Rehkemper et al.

(10) Patent No.: US 6,622,333 B1
(45) Date of Patent: Sep. 23, 2003

(54) PNEUMATIC-OPERATED TOOTHBRUSH

(75) Inventors: Steven Rehkemper, Chicago, IL (US); Jeffrey Rehkemper, Chicago, IL (US); Charles Hartlaub, Glendale Heights, IL (US); Todd Hannon, Burlington, WI (US)

(73) Assignee: Rehco, LLC, Chicago, IL (US)

( * ) Notice: Subject to any disclaimer, the term of this patent is extended or adjusted under 35 U.S.C. 154(b) by 0 days.

(21) Appl. No.: 10/233,687

(22) Filed: Sep. 4, 2002

(51) Int. Cl.$^7$ .......................... A61C 17/32; A46B 13/00
(52) U.S. Cl. .................. 15/29; 15/22.1; 15/22.2; 15/28
(58) Field of Search ................ 15/22.1, 22.2, 15/23, 24, 28, 29

(56) References Cited

U.S. PATENT DOCUMENTS

| | | | |
|---|---|---|---|
| 1,971,283 A | * 8/1934 | Stimson | ..................... 15/24 |
| 3,144,867 A | 8/1964 | Trupp et al. | |
| 4,146,020 A | 3/1979 | Moret et al. | |
| 4,181,997 A | 1/1980 | O'Rourke | |
| 4,223,417 A | 9/1980 | Solow | ..................... 15/22.1 |
| 4,257,433 A | 3/1981 | Kwan | |
| 4,321,722 A | * 3/1982 | Klocke | ..................... 15/29 |
| 4,346,492 A | 8/1982 | Solow | ..................... 15/22.1 |
| 4,412,823 A | 11/1983 | Sakai et al. | |
| 4,660,244 A | 4/1987 | Polyak | |
| 4,845,795 A | 7/1989 | Crawford et al. | ............ 15/22.1 |
| 4,958,629 A | 9/1990 | Peace et al. | |
| 4,979,503 A | 12/1990 | Chernack | |
| 5,142,723 A | 9/1992 | Lustig et al. | |
| 5,286,192 A | 2/1994 | Dixon | |
| 5,304,010 A | 4/1994 | Hsing-San | |
| 5,341,534 A | 8/1994 | Serbinski et al. | ............ 15/22.1 |
| 5,500,973 A | 3/1996 | Phelan | |
| 5,524,312 A | 6/1996 | Tan et al. | ..................... 15/22.1 |
| 5,640,735 A | 6/1997 | Manning | |
| 5,683,192 A | 11/1997 | Kilfoil | |
| 6,000,083 A | 12/1999 | Blaustein et al. | ............... 15/28 |
| 6,030,215 A | 2/2000 | Ellion et al. | |
| 6,047,429 A | 4/2000 | Wu | |
| 6,178,579 B1 | 1/2001 | Blaustein et al. | ............... 15/28 |
| 6,189,693 B1 | 2/2001 | Blaustein et al. | ......... 206/362.2 |
| 6,311,837 B1 | 11/2001 | Blaustein et al. | ......... 206/362.2 |
| 6,331,088 B2 | 12/2001 | Owens | |

FOREIGN PATENT DOCUMENTS

| | | | | |
|---|---|---|---|---|
| CA | 730840 | * | 3/1966 | ................. 15/22.1 |
| FR | 340683 | * | 7/1904 | ..................... 15/29 |
| JP | 09322823 | | 12/1997 | |
| WO | WO00/41645 | | 7/2000 | |

* cited by examiner

Primary Examiner—Mark Spisich

(57) ABSTRACT

In accordance with one embodiment of the present invention a pneumatic-operated toothbrush incorporates a pump that a user may utilize to pump are into and pressurize air in a reservoir. The reservoir is attached to a pneumatic motor, which utilizes the pressurized air inside the reservoir to rotate a drive shaft. Attached to the end of the drive shaft is a plurality of bristles that rotate when the drive shaft is rotating. The motor will continue to rotate the bristles as long as the pressure inside the reservoir is sufficient enough to force the air into the pneumatic motor. When the motor stops rotating the bristles, the user can pump air back inside the reservoir for continued use. It is important to note that the pneumatic toothbrush for the present invention is a self-contained device, meaning that the reservoir, motor and pump are incorporated into a single toothbrush. In addition the present invention does not use batteries or other electrical elements to power the motor.

16 Claims, 7 Drawing Sheets

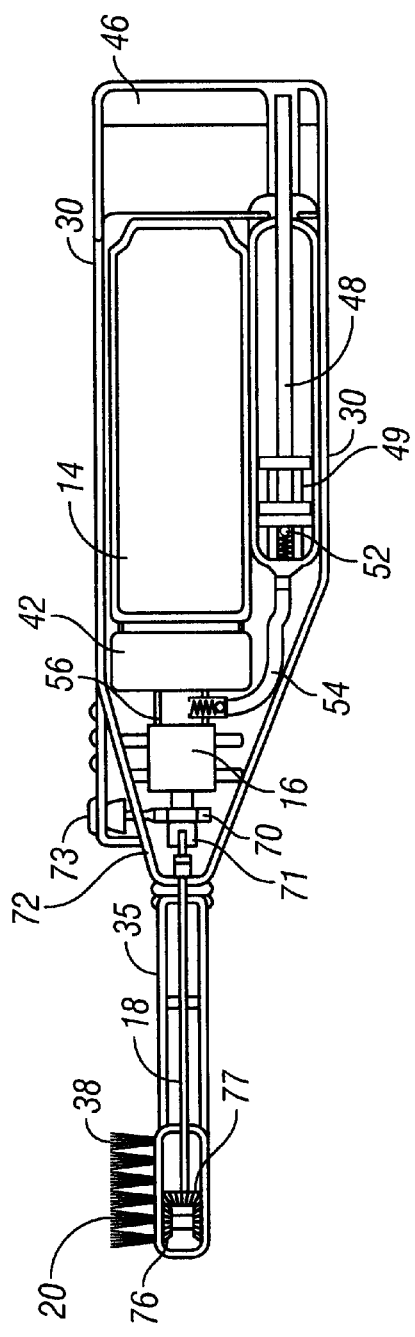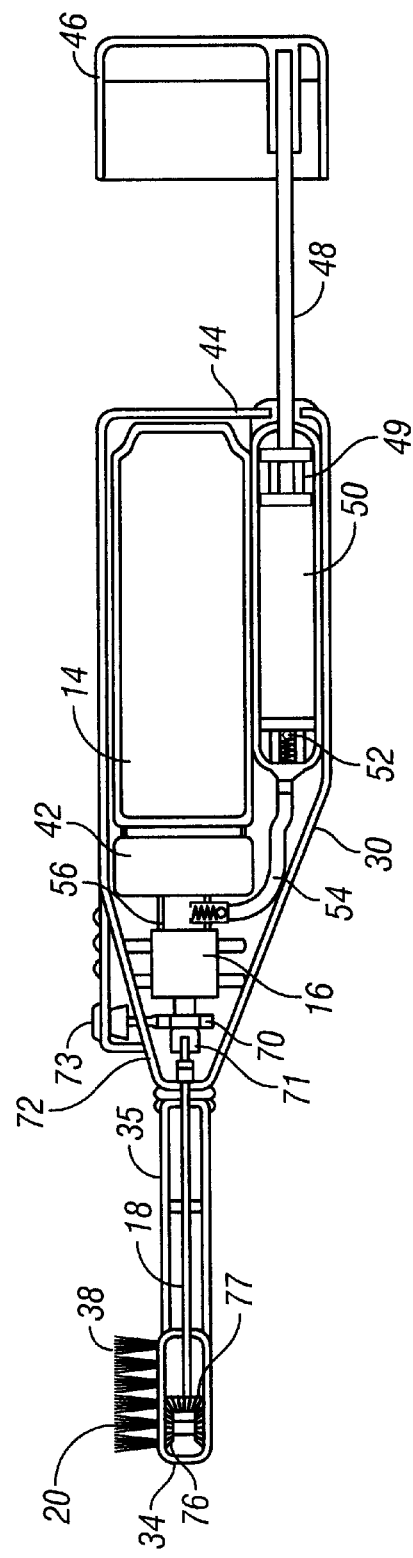

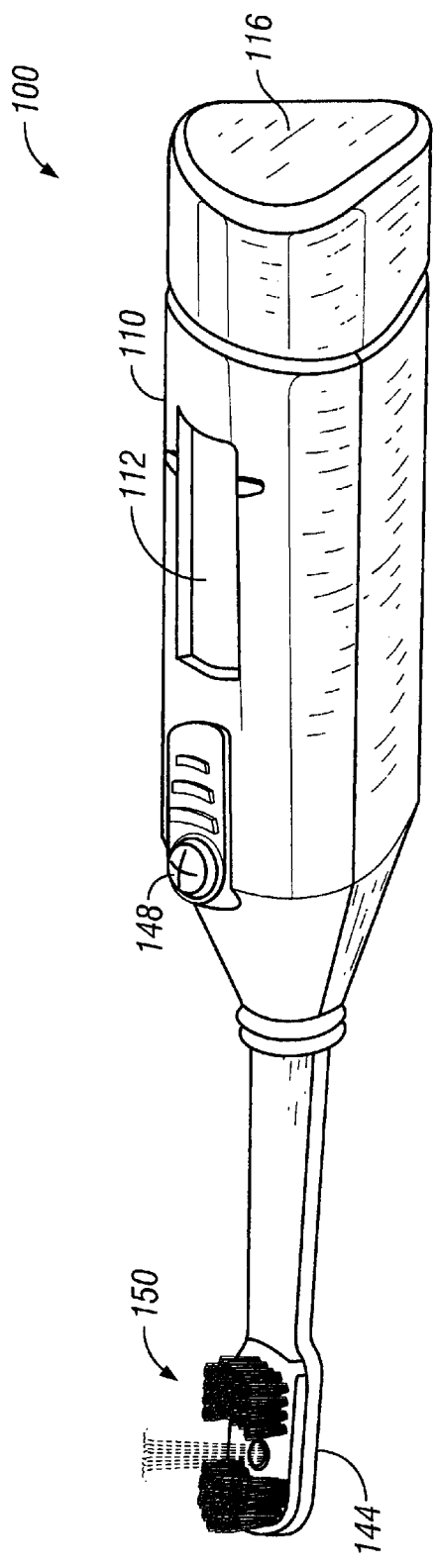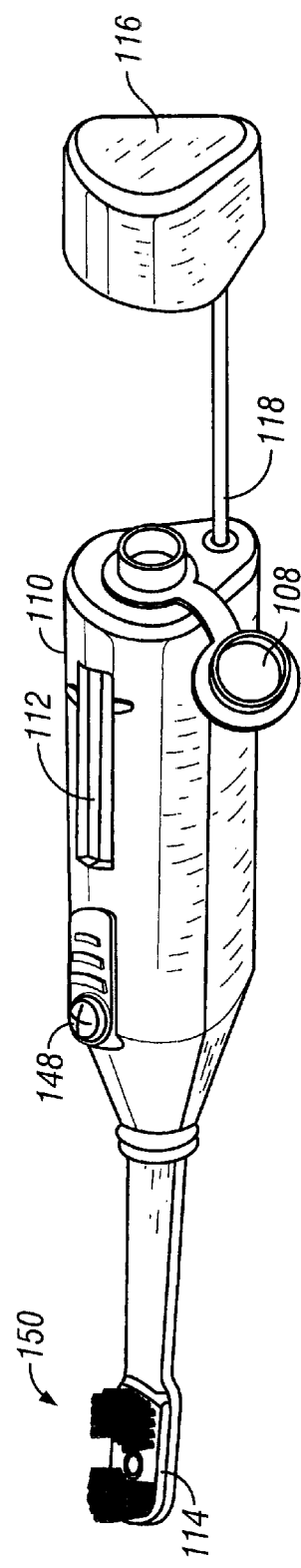

PNEUMATIC-OPERATED TOOTHBRUSH

FIELD OF THE INVENTION

The present invention relates to portable toothbrushes, and in particular to self-contained pneumatic-operated toothbrushes that utilized pressured fluids to move bristles and/or to spray water to aid a user brushing, cleaning and/or rinsing their teeth.

BACKGROUND OF THE INVENTION

The ability for a user to clean their teeth with a typical toothbrush relies solely on the brushing technique of the user. Various cleaning instruments, such as electric toothbrushes have been provided to augment the brushing such that the ability to clean relies less on the user's technique to clean their teeth. For example, U.S. Pat. No. 6,189,693; U.S. Pat. No. 5,341,534, and U.S. Pat. No. 5,524,312, provide for electric/mechanical toothbrushes, which help augment the brushing technique. These mechanical toothbrushes commonly use a DC motor to rotate or move bristles such that a user holding the toothbrush over their teeth will be able to allow the mechanical toothbrush to do most of the work for them. However, these mechanical toothbrushes far short of providing an inexpensive means of replacing non-mechanical toothbrushes. Also, since mechanical toothbrushes are typically more expensive then non-mechanical toothbrushes, mechanical toothbrushes usually employ removable heads that may be replaced when worn or utilize replaceable batteries. In yet other prior art mechanical toothbrushes, the motors or batteries can be charged by a conventional power cord that may be inserted into a typical inlet; such as the mechanical toothbrush disclosed in U.S. Pat. No. 4,845,795. However, without access to an inlet, these mechanical toothbrushes will not receive any power to function properly.

Other mechanical toothbrushes have been provided in U.S. Pat. Nos. 4,346,492 and 4,223,417 issued to Solow. The Solow patents provide pneumatically driven tufts of bristles that are pushed perpendicularly against a person's teeth. One problem with the Solow patents is that the tuft of bristles stops when bristles impact the teeth. It is therefore easy for a few bristles to contact the teeth and slow down or even stop the action of the piston preventing the rest of the bristles to contact the teeth. As such, the Solow patents fail to provide an adequate means to brush a user's teeth.

Since the advent of mechanical toothbrushes other means have been provided to assist or augment the cleaning or rinsing of the user's teeth, such as the use of water to pick at, spray, or rinse the teeth. For example, U.S. Pat. No. 6,047,429 uses a water jet in combination with a mechanical toothbrush. The motor used to move the bristles is also used to pump water from an outside source, not contained within the toothbrush. The water is pumped from the outside source through the neck of the toothbrush and out of the head of the toothbrush at a user's teeth. U.S. Pat. No. 5,304,010 incorporates a toothbrush that is tethered to a faucet to provide a stream of water for rinsing. Various problems in these and other similar prior art water jet toothbrushes are the fact that the toothbrush must be tethered or connected to an outside source of water.

As such there still exists the need to provide a user with a completely portable handheld self-contained toothbrush that properly assists the user in brushing their teeth. The toothbrush should provide an effective means of augmenting the user's technique in brushing their teeth, by providing a toothbrush that incorporates moving bristles. Such a toothbrush should further eliminate the need for intricate or complicated means to move the bristles. The toothbrush may further provide the ability for the user to spray water on the teeth to assist the cleaning or rinsing of the teeth, without the need for tethering the toothbrush to an outside source of water and/or other power supply.

SUMMARY OF THE INVENTION

In accordance with one embodiment of the present invention a handheld portable self-contained toothbrush is provided that incorporates an on-board pump that a user may use to force or pump fluid, especially air into a storage means or reservoir. Repeatedly pumping by the user will pressurize the air there-inside. The reservoir is attached to a pneumatic motor, which when activated, utilizes the pressurized air inside the reservoir to move a plurality of bristles that are in communication therewith. As long as there remains pressurized air inside the reservoir the pneumatic motor will move the bristles. When the air is exhausted or there is insufficient amount of pressurization to operate the pneumatic motor, the movement the bristles slows or stops. The user may then repeat the process by pumping air back into the reservoir for continued use. In the present invention, the reservoir may be any type of holding facility such as a plastic or metal bottle or a latex bladder.

In another embodiment, a toothbrush is provided with an on-board pump that is used to pressurize a refillable chamber of water. The pressurized water may then be sprayed out of the toothbrush to assist in cleaning the user's teeth.

In yet another embodiment, a toothbrush is provided with an on-board pump to pressurize a chamber of air and to pressurize a refillable chamber of water. The pressurized air is used to operate a pneumatic motor that is in communication with and moves a plurality of movable bristles. The pressurized water exits the head of the toothbrush such that the user may also use the pressurized water to help clean or rinse their teeth.

The present invention may also incorporate a means for starting the movement of the bristles, such as a mechanism that when depressed allows the pneumatic motor to begin moving the bristles. Such a starting means will help prevent the pneumatic motor from running while the user is pressurizing the fluid contained in the toothbrush. However, other starting means may be employed, as further mentioned in the Detailed Description of the Invention, hereinbelow.

Numerous other advantages and features of the invention will become readily apparent from the following detailed description of the invention and the embodiments thereof, from the claims, and from the accompanying drawings.

BRIEF DESCRIPTION OF THE DRAWINGS

A fuller understanding of the foregoing may be had by reference to the accompanying drawings, wherein:

FIG. 3 is a cross-sectional view of the pneumatic operated toothbrush of FIG. 1 with the pump handle pushed inwardly;

FIG. 4 is a cross-sectional view of the pneumatic operated toothbrush of FIG. 1 with the pump handle extended away from the toothbrush;

FIG. 5 is a perspective view of a second embodiment of a toothbrush that includes the ability to eject pressurized water;

FIG. 6 is a perspective view of FIG. 5 with the pump handle extended such that a user may fill the water chamber;

DETAILED DESCRIPTION OF THE EMBODIMENTS

Figure 1:
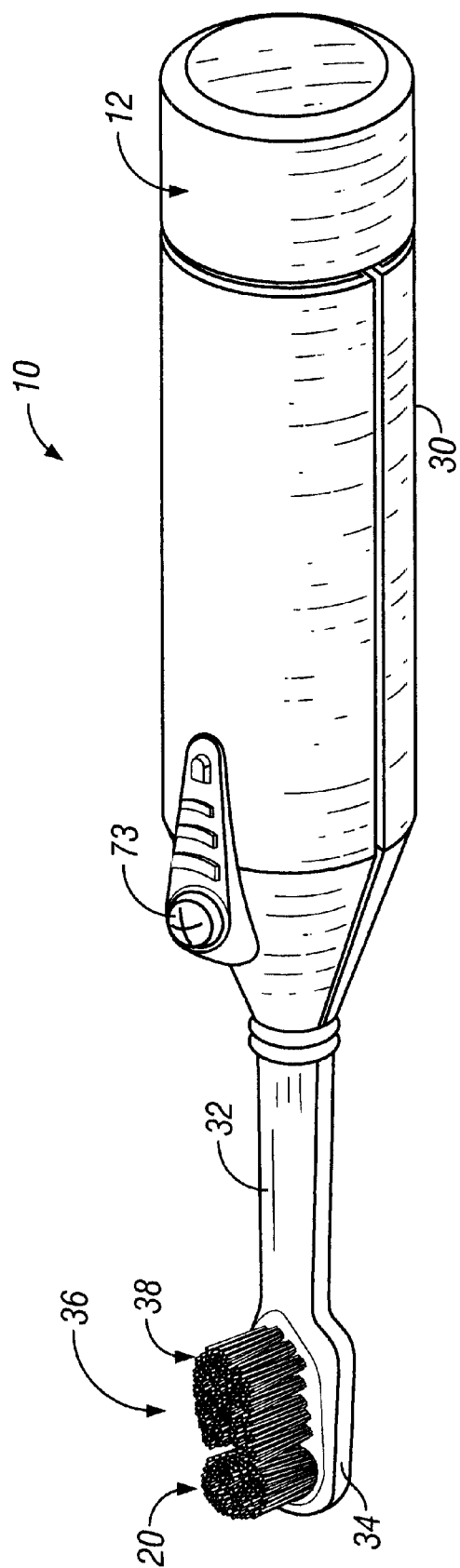
FIG. 1 is a perspective view of a first embodiment of a pneumatic operated toothbrush having a pump attached thereto for pumping air into and pressurizing air in a reservoir, wherein the pressurized air is used to operate or rotate a plurality of bristles.

While the invention is susceptible to embodiments in many different forms, there are shown in the drawings and will be described herein, in detail, the preferred embodiments of the present invention. It should be understood, however, that the present disclosure is to be considered an exemplification of the principles of the invention and is not intended to limit the spirit or scope of the invention and/or claims of the embodiments illustrated.

Referring now to FIGS. 1 through 4, there is disclosed in accordance with a first embodiment of the present invention a pneumatic toothbrush generally referenced to as numeral 10. The pneumatic toothbrush 10 incorporates a pump 12 that a user may force or pump air into a storage means. Repeatedly pumping air into the storage means will pressurize the air there-inside. The storage means is further attached to a pneumatic motor. When activated, the pneumatic motor utilizes the pressurized air inside the storage means to rotate a drive shaft. In communication with the drive shaft is a plurality of bristles 20 that rotate when the drive shaft is rotating. When the air is exhausted or the pressure inside the storage means is significantly reduced, the motor will no longer rotate the bristles. However, the user can pump air back into the storage means for continued use.

Continuing to refer FIG. 1, the toothbrush 10 is similar to other handheld mechanical toothbrushes in that it includes a body 30 that houses the other components of the toothbrush 10. Extending outwardly from the body 30 is a neck 32 for which a head 34 further extends therefrom. A plurality of bristles 36 is further attached to the head 34. The present invention may incorporate a plurality of non-moving bristles 38 and plurality of moving or rotating bristles 20 or may only include moving bristles.

Figure 2:
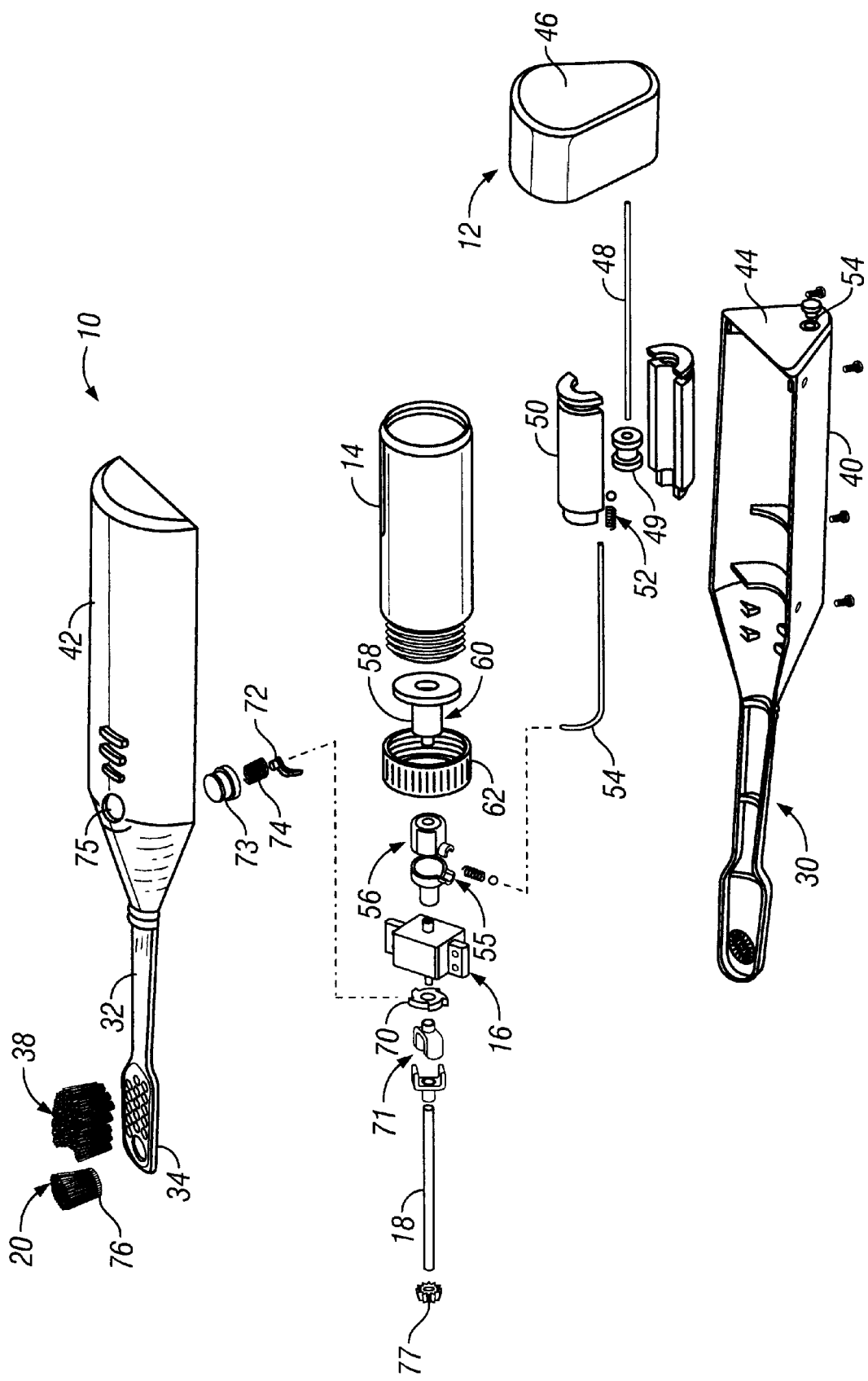
FIG. 2 is an exploded view of the pneumatic operated toothbrush of FIG. 1.

Referring now also to FIG. 2, the body 30 of the toothbrush 10 is a two-piece molded housing 40 and 42 representing a back half and a front half respectively. The toothbrush 10 may further be separated into a detachable head or neck or incorporate removable bristles, which would allow a user to replace worn toothbrushes with new bristles without having to replace the entire toothbrush. In any regard, the present invention as mentioned previously includes a neck 32, extending away from the body 30, and a head 34 attached to the end of the neck 32, for receiving a plurality of bristles 36, which include moving 20 and/or nonmoving 38.

Attached to the body 30 is the pump 12, which allows a user to pump air into and pressurize air in the storage means or a reservoir 14, which is housed within the body 30 of the toothbrush 10. The pump 12 includes a pump handle 46, a pump piston 48 and a corresponding pump cylinder 50. The pump piston 48 slides through an aperture 54 formed in a portion 44 of the body 30. Attached to the end of the pump piston 48 is a pump seal 49 that helps push air through the pump cylinder 50. When air is pumped through the pump cylinder 50 the air passes a one-way valve 52, such as a well known ball/spring valve, which prevents air from re-entering the pump cylinder 50. The air travels through an air tube 54 that leads to a second one-way valve 55 and into an inlet chamber 56. As the air is being pumped into the inlet chamber 56 the air is forced into the reservoir 14, because the pneumatic motor 16 is initially not operating, discussed in greater detail below. The air enters the reservoir 14 by traveling through a fluid channel 58 that is in fluid communication with the inlet chamber 56 and the reservoir 14. To prevent the reservoir 14 from leaking, a seal cap 62 seals the reservoir 14. The inlet chamber 56 is also in fluid communication with the pneumatic motor 16.

As briefly mentioned above, to fill the reservoir 14 with air, the user pulls the pump handle 46 away from the toothbrush 10 extending the pump piston 48 out of the pump cylinder 50 as illustrated in FIG. 4, and then pushes the pump handle 46 towards the toothbrush 10, compressing the pump piston 48 into the pump cylinder 50, as illustrated in FIG. 3, forcing air through the pump cylinder 50 and into the reservoir 14.

Like other known pneumatic motors, the present invention incorporates a pneumatic motor 16 that utilizes the pressurized air to rotate an axle (not shown). In addition, the pneumatic motor 16 is preferably designed such that it is automatically running when air is initially pumped into the reservoir. However, to conserve the pressurized air until the user is ready or to allow the user to fill the reservoir 14 without wasting pressurized air, the present invention includes a means that prevents the bristles 20 from rotating as well as a means to release such preventing means.

Continuing to refer to FIG. 2, secured to the axle is a ratchet gear 70 that is also in communication with a pawl 72. A starter button 73 and a compression spring 74 are placed such that the compression spring 74 will position the pawl 72 to engage the ratchet gear 70, preventing the axle from rotating. The starter button 73 is further positioned through an opening 75 in the top half 42 of the body 30. A user pressing the starter button 73 will move the pawl 72 such that the ratchet gear 70 may rotate, thus releasing the axle. Moreover, the user releasing the starter button 73 will cause the pawl 72 to re-engage the ratchet gear 70. This permits the user to have in essence a mechanical on/off switch. However, it should be readily apparent that other means may be employed to start and stop the bristles. Moreover, the present invention may not include any means, allowing the bristles to always rotate when pressurized air is in the reservoir, even when the reservoir is being filled.

Attached onto the axle past the ratchet gear 70, is a link joint 71 that attaches the drive shaft 18 to the axle. The drive shaft 18 is positioned in the neck 32 of the toothbrush 10 and connects to a head gear 77. The head gear 77 is positioned directly under the rotating bristles 20, in the head 34 of the toothbrush 10. A crown gear 76, best seen in FIGS. 3 and 4, is molded underneath the rotating bristles 20. The crown gear 76 engages the head gear 77, such that when the head gear 77 rotates counterclockwise in the vertical plane, the crown gear 76 rotates counterclockwise in the horizontal plane.

Figure 7:
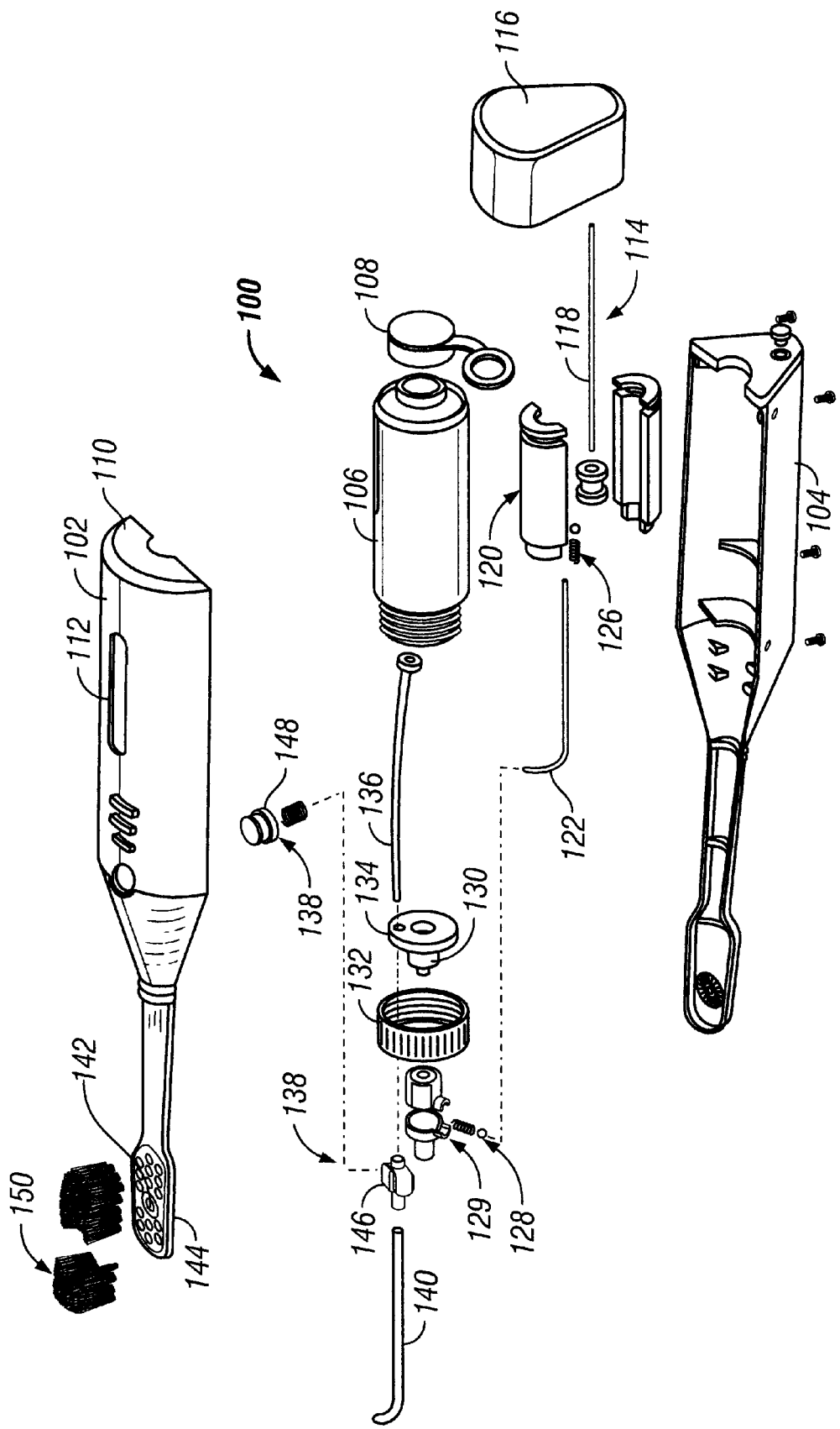
FIG. 7 is an exploded view of FIG. 5.

Referring now to FIGS. 5 through 7, another embodiment of the present invention is illustrated. A toothbrush 100 is provided with the ability to use pressurized water to assist a user in brushing their teeth. The toothbrush 100 is preferably a two piece construction 102 and 104 that when assembled houses the various components. The toothbrush 100 includes a water chamber 106 contained within the toothbrush 100. The water chamber 106 is refillable through the removable cap 108 that is accessible from outside of the toothbrush 100, preferably in the bottom section 110 of the toothbrush, as viewed when the toothbrush is positioned upright, illustrated in FIG. 6. The user may be able to determine how much water is in the chamber through an integrated window 112 in one of the pieces 102 of the toothbrush housing. After filling the water chamber 106 the user may pressurize the water inside by pumping air into the water chamber 106, by using a pump 114.

The pump 114 is similarly constructed to the pump in the first embodiment. The pump 114 includes a pump handle 116 attached to a pump piston 118, which pushes air through a pump cylinder 120, into an air tube 122 and then into an inlet chamber 124. Two one-way valves 126 and 128 are separately positioned between the pump cylinder 120 and the air tube 122 and between the air tube 122 and the inlet chamber 124, respectively. The air entering the inlet chamber 124 will then enter the water chamber 106 through an air channel 130 defined in a seal 134. The water chamber 106 is further secured to the inlet chamber 124 by a chamber cap 132.

Once the water chamber 106 has water and pressurized air, the water is forced through a water tube 136 that is in fluid communication with the inside of the water chamber 106. The water tube 136 leads from the water chamber 106 through the seal 134 to a preventing/activation means 138 that permits the user to control when the water will eject from the toothbrush 100. In fluid communication with the preventing/activation means 138 is a second water tube 140 that leads to an opening 142 in the head 144 of the toothbrush 100.

The a preventing/activation means 138 could be a valve mechanism 146 that is activated by a button 148, or other well known means may be employed. When the water chamber 106 contains the pressurized water, the user may activate the preventing/activation means 138 such that the pressurized water exits the bristles 150 upwardly, allowing the user to use the pressurized water to assist in cleaning the user's teeth. In addition, the user may deactivate the preventing/activation means 138, such that the remaining pressurized water may be saved and used at a later time.

As mentioned above in the previous embodiment the neck of the pneumatic toothbrush may be removed to replace worn bristles. However, the toothbrush 100 incorporating pressurized water may include removable tops or neck/head assemblies to accommodate various cleaning attachments. For example, the illustrated neck/head assembly showing the bristles that include spraying water could be replaced with a neck/head assembly that does not include bristles but is a straight water pick, meaning it only sprays water. Alternatively a neck/head assembly may be made that is used to brush a user's tongue.

Figure 8:
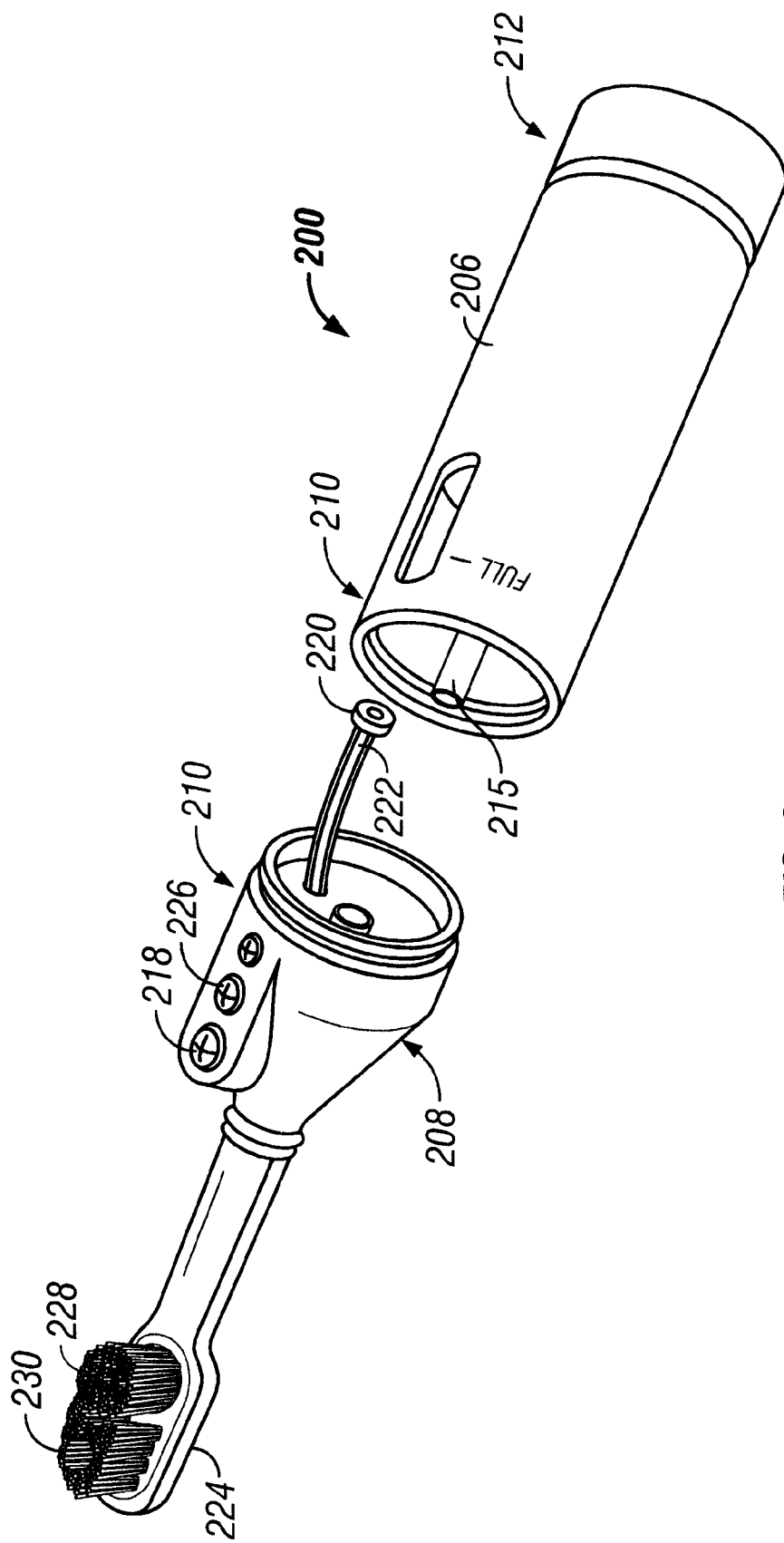
FIG. 8 is a perspective view of another embodiment of the present invention that includes two reservoirs for separately holding water and pressurized air, such that the toothbrush may have rotating bristles operated by a pneumatic motor and a water pick.
Figure 9:
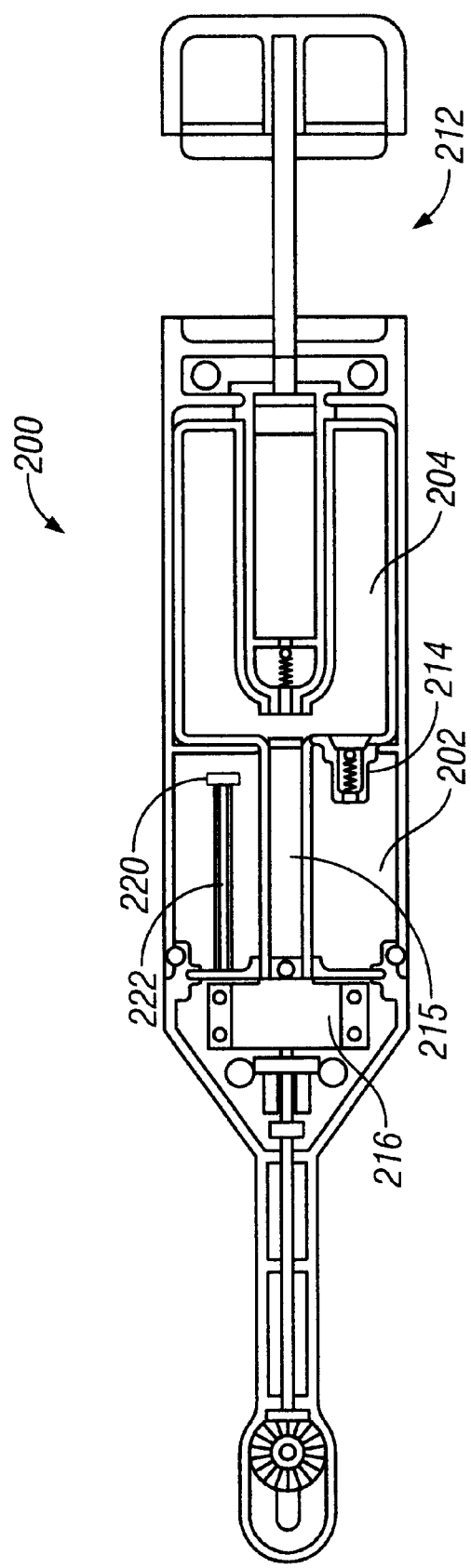
FIG. 9 is a cross section view of FIG. 8.

Referring now to FIGS. 8 and 9, another embodiment of a pneumatic operated toothbrush is disclosed and referred to as numeral 200. In this embodiment the pneumatic toothbrush 200 has two chambers, an air chamber 202 that will hold pressurized air and a water chamber 204 that will hold pressurized water. A user first fills the water chamber 204 with regular or un-pressurized water. Various filling means may be utilized, such as the ability to screw a bottom section 206 away from a top section 208 from the body 210 of the toothbrush 200. In addition, other filing means described above may be incorporated. The user then begins to pump air into and pressurize air in the air chamber 202, by utilizing a pumping means 212. A check valve 214 attached between the air chamber 202 and the water chamber 204 allows pressurized air to enter the water chamber 204, when the user is pumping air into the air chamber 202, such that the water inside the water chamber 204 can be forced out. This is caused when the user continues to pump air into the air chamber 202. After the air chamber 202 reaches a pressure greater then the pressure of the water the air is able flow through the check valve 214 such that pressurized air can enter the water chamber 204.

The toothbrush 200 also includes an air channel 215 leading from the air chamber 202 to a pneumatic motor 216, such that the pneumatic motor 216 may utilize the pressurize air to operate, in a manner discussed hereinabove in the other embodiments. As such the toothbrush 200 may include a means to prevent the pneumatic motor from operating as well as a releasing means. The releasing means may be activated through a release button 218 accessible from the outside of the toothbrush.

The water chamber 204 includes a water inlet 220, which attaches to a water tube 222. The water tube 222 runs from the water chamber 204 to head 224 of the toothbrush 200, such that the pressurized water exits the toothbrush 200 in a manner that permits the user to use the pressurized water to help clean the user's teeth. The toothbrush 200 may further include a means to prevent and allow the ejection of pressurized water. The means to allow the ejection of water may be activated, separately from the activation of the pneumatic motor, as such a button 226 is also provided to activate the water pick.

As defined in the previous embodiments, the pneumatic motor when operating rotates a drive shaft that further rotates a plurality of bristles 228. The water however, is ejected through a plurality of non-rotating bristles 230.

It is also important to note that the embodiments disclosed herein cover a pneumatic toothbrush that is a self contained device, meaning that the components, namely the storage means, motor mechanism and pump means are incorporated into a single toothbrush. In addition the present invention does not use batteries or other electrical means to power the motor. It should be further noted, that while embodiments disclose a plurality of rotating bristles, the present invention may also include the ability to move the bristles in other fashions, such as in a reciprocating motion.

From the foregoing and as mentioned above, it will be observed that numerous variations and modifications may be effected without departing from the spirit and scope of the novel concept of the invention. It is to be understood that no limitation with respect to the specific methods and apparatus illustrated herein is intended or inferred. It is intended to cover by the appended claims all such modifications as fall within the scope of the claims.

We claim:

1. A pneumatic toothbrush having a body which a user may grasp, a neck extending outwardly from the body and a head for holding bristles, the head extending from the neck, the pneumatic toothbrush further comprising:

a reservoir housed within the body of the pneumatic toothbrush;

a means to pump air into the reservoir, wherein repeatedly pumping air into the reservoir will pressurize the air there-inside, said pump means attached to the body of the pneumatic toothbrush;

a pneumatic motor housed within the body of the pneumatic toothbrush and in fluid communication with the reservoir, said pneumatic motor when running, utilizes pressurized air inside the reservoir to rotate a drive shaft extending outwardly from the pneumatic motor, the drive shaft rotatably contained in the neck; and a plurality of bristles held in the head and meshed to the drive shaft such that the plurality of bristles move, when the drive shaft is rotating.

2. The pneumatic toothbrush of claim 1, wherein the pneumatic motor runs when the reservoir includes pressurized air.

3. The pneumatic toothbrush of claim 2 further comprising a mechanical means to prevent the pneumatic motor from running thereby preventing the bristles from moving.

4. The pneumatic toothbrush of claim 3 further comprising a mechanical means to release the prevent means.

5. The pneumatic toothbrush of claim 4, wherein the prevent means includes a ratchet gear secured to the drive shaft and a pawl positioned to engage the ratchet gear.

6. The pneumatic toothbrush of claim 5, wherein the release means includes a starter button in communication with said pawl such that when the starter button is pressed the pawl disengages the ratchet gear permitting the pneumatic motor to rotate the drive shaft and thus move the bristles.

7. The pneumatic toothbrush of claim 6, wherein the release means also includes a compression spring that causes the pawl to re-engage the ratchet gear when the button is released.

8. The pneumatic toothbrush of claim 1, wherein the pump means includes a pump cylinder secured within the body of the toothbrush and in fluid communication with the reservoir, and a pump piston having an end that fits into the pump cylinder to create a fluid tight relationship therewith and having an other end attached to a pump handle, such that a user may push and pull the pump piston through the pump cylinder pumping air into the reservoir.

9. A pneumatic toothbrush comprising:

a reservoir contained within a body defined by the pneumatic toothbrush;

a on-board pump attached to the body and in fluid communication with the reservoir such that air can be pumped into the reservoir and air inside the reservoir can be pressurized;

a pneumatic motor housed within the body and in fluid communication with the reservoir, the pneumatic motor utilizes the pressurized air inside the reservoir to rotate a drive shaft; and a plurality of movable bristles that move when the drive shaft rotates.

10. The pneumatic toothbrush of claim 9 further comprising a mechanical means to prevent the pneumatic motor from running thereby preventing the bristles from rotating, the prevent means includes a ratchet gear secured to the drive shaft and a pawl positioned to engage the ratchet gear.

11. The pneumatic toothbrush of claim 10 further comprising a mechanical means to release the prevent means, the release means includes a starter button in communication with said pawl such that when the starter button is pressed the pawl disengages the ratchet gear permitting the pneumatic motor to rotate the drive shaft and thus rotate the bristles and also includes a compression spring that causes the pawl to reengage the ratchet gear when the button is released.

12. A pneumatic toothbrush having a body which a user may grasp, a neck extending outwardly from the body and a head attached with the neck for holding bristles, the toothbrush further comprising:

a water storage means for holding water, the water storage means housed within said body;

an air storage means for holding air, the air storage means also housed within said body;

a valve in communication between the water storage means and the air storage means, said valve having a means to prevent water from entering the air storage means from the water storage means and further having a means that allows air to entering the water storage means from the air storage means;

a means for filling the water storage means with water;

a means to pump air into the air storage means, wherein repeatedly pumping air into the air storage means will pressurize the air inside the air storage means and pressurize the water inside the water storage means, said pump means attached to the body of the pneumatic toothbrush;

a motor mechanism housed within said body and in fluid communication with the air storage means, said motor mechanism when running, utilizes pressurized air inside the air storage means to rotate a drive shaft extending outwardly from the motor mechanism, the drive shaft being housed in the neck, a plurality of bristles held in the head and meshed to the drive shaft such that the plurality of bristles rotate, when the drive shaft is rotating; and an outlet for exhausting the pressurized water, a tube connected to the outlet leads from the water storage means to an aperture in the head of the toothbrush such that pressurized water exits the toothbrush from said aperture.

13. The toothbrush of claim 12 further comprising a means to activate the motor mechanism, wherein upon activation the motor mechanism will continue to run until the pressure of the air in the air storage means is insufficient to operate the motor mechanism.

14. The pneumatic toothbrush of claim 12 further comprising a means to allow and prevent the pressurized water from exiting the toothbrush.

15. The toothbrush of claims 1, 8, 9, or 12 further comprising a plurality of non-rotating bristles.

16. The toothbrush of claim 15 wherein the plurality of non-rotating and movable bristles are replaceable.

* * * * *